US012070583B2

(12) United States Patent
Roy (10) Patent No.: US 12,070,583 B2
(45) Date of Patent: *Aug. 27, 2024

(54) FLUID INJECTION DEVICES AND RELATED METHODS

(71) Applicant: MEDTRONIC MINIMED, INC., Northridge, CA (US)

(72) Inventor: Anirban Roy, Agoura Hills, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 190 days.

This patent is subject to a terminal disclaimer.

(21) Appl. No.: 17/521,443

(22) Filed: Nov. 8, 2021

(65) Prior Publication Data

US 2022/0062559 A1    Mar. 3, 2022

Related U.S. Application Data

(63) Continuation of application No. 16/566,814, filed on Sep. 10, 2019, now Pat. No. 11,173,251, which is a
(Continued)

(51) Int. Cl.
*A61M 5/315* (2006.01)
*A61M 5/172* (2006.01)
(Continued)

(52) U.S. Cl.
CPC ...... *A61M 5/31546* (2013.01); *A61M 5/1723* (2013.01); *A61M 5/20* (2013.01); *A61M 5/24* (2013.01); *G16H 20/17* (2018.01)

(58) Field of Classification Search
CPC .. A61M 5/31546; A61M 5/1723; A61M 5/24; A61M 5/20; G06F 19/30
See application file for complete search history.

(56) References Cited

U.S. PATENT DOCUMENTS

| 4,755,173 A | 7/1988 | Konopka et al. |
| 5,391,250 A | 2/1995 | Cheney, II et al. |

(Continued)

OTHER PUBLICATIONS

Bolus Insulin Basics, Extra Insulin When Your Body Needs It, OmniPod, Insulin Management System, Retrieved from the Internet: URL: http://www.myomnipod.com/managing-diabetes/about-pump-therapy/bolus basics/ [Retrieved on Mar. 26, 2015].

(Continued)

*Primary Examiner* — Bradley J Osinski
(74) *Attorney, Agent, or Firm* — Weaver Austin Villeneuve & Sampson LLP (57) ABSTRACT

Fluid injection devices and related systems and operating methods are provided. An exemplary injection device includes an actuation arrangement to facilitate delivering fluid from a container, a user interface element coupled to the actuation arrangement, a data storage element to maintain one or more patient-specific parameter values and historical bolus data, and a control module coupled to the actuation arrangement and the data storage element. The control module of the injection device determines a bolus amount of the fluid to be delivered based at least in part on the one or more patient-specific parameter values and the historical bolus data in response to receiving a user input indicative of a desire to administer a bolus, and the control module configures the actuation arrangement to automatically deliver the bolus amount in response to manual actuation of the user interface element.

20 Claims, 3 Drawing Sheets

Related U.S. Application Data continuation of application No. 14/670,124, filed on Mar. 26, 2015, now Pat. No. 10,449,298.

(51) Int. Cl.
*A61M 5/20* (2006.01)
*A61M 5/24* (2006.01)
*G16H 20/17* (2018.01)

(56) References Cited

U.S. PATENT DOCUMENTS

| | | | |
|---|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 10,232,113 B2 | 3/2019 | Palerm |
| 10,265,031 B2 | 4/2019 | Palerm et al. |
| 10,307,535 B2 | 6/2019 | Palerm et al. |
| 10,449,298 B2 | 10/2019 | Roy |
| 11,173,251 B2 | 11/2021 | Roy |
| 2003/0163088 A1* | 8/2003 | Blomquist ............ G16H 20/17 700/282 |
| 2005/0192557 A1 | 9/2005 | Brauker et al. |
| 2007/0123819 A1 | 5/2007 | Mernoe et al. |
| 2009/0253973 A1* | 10/2009 | Bashan ................ G16H 10/00 604/67 |
| 2010/0160861 A1 | 6/2010 | Causey, III et al. |
| 2010/0191075 A1* | 7/2010 | Angelides ............ G16H 20/10 709/219 |
| 2011/0275986 A1 | 11/2011 | Bashan et al. |

OTHER PUBLICATIONS

The Smart Insulin Pen, Diabetesnet.com, Retrieved from the Internet: URL: http://www.diabetesnet.com/diabetes-technology/Blueskying/smart-insulin-pen [Retrieved on Mar. 26, 2015].

* cited by examiner

FLUID INJECTION DEVICES AND RELATED METHODS

CROSS-REFERENCE TO RELATED APPLICATIONS

This application is a continuation of U.S. patent application Ser. No. 16/566,814, filed Sep. 10, 2019, which is a continuation of U.S. patent application Ser. No. 14/670,124, filed Mar. 26, 2015, now issued U.S. Pat. No. 10,449,298.

TECHNICAL FIELD

Embodiments of the subject matter described herein relate generally to medical devices, and more particularly, embodiments of the subject matter relate to fluid injection devices used to manually administer dosages, such as insulin pens.

BACKGROUND

Fluid injection devices, such as insulin pens, are relatively well known in the medical arts, for use in delivering or dispensing an agent, such as insulin or another prescribed medication, to a patient. Typical insulin pens must be physically manipulated by a user to configure a desired dosage, with that desired dosage often being manually calculated or determined by the user. However, the amount of manual interaction required poses a risk of human error, for example, when manually determining the proper dosage amount and/or when manually operating the pen to self-administer that desired dosage, and such risks may be further exacerbated if the user is experiencing a hypoglycemic or hyperglycemic event. Accordingly, it is desirable to provide injection pens that are capable of accurately and reliably delivering a specific dosage in a simplified manner that reduces the workload on the user.

BRIEF SUMMARY

Fluid injection devices, systems and related methods of operation in accordance with various operating modes are provided. An exemplary injection device includes an actuation arrangement to facilitate delivering fluid from a container, a user interface element coupled to the actuation arrangement, a data storage element to maintain one or more patient-specific parameter values and historical bolus data, and a control module coupled to the actuation arrangement and the data storage element. The control module determines a bolus amount of the fluid to be delivered based at least in part on the one or more patient-specific parameter values and the historical bolus data in response to receiving a user input indicative of a desire to administer a bolus. After the bolus amount is determined, the control module configures the actuation arrangement to automatically deliver the bolus amount in response to actuation of the user interface element.

In another embodiment, a method of operating an injection pen to deliver fluid to a patient is provided. The method involves receiving user input indicative of a desire to administer a bolus using the injection pen, and after receiving the user input, determining, by the injection pen, a bolus delivery amount of the fluid based at least in part on one or more parameter values associated with the patient and historical bolus data associated with previous boluses delivered to the patient using the injection pen. Thereafter, the injection pen configures its actuation arrangement to automatically deliver the bolus delivery amount in response to actuation of a user interface element of the injection pen.

In another embodiment, an insulin injection pen is provided. The insulin injection pen includes an actuation arrangement to facilitate delivering insulin from a container to a body of a patient, a delivery button coupled to the actuation arrangement, and a data storage element to maintain parameter values associated with the patient and historical bolus data for the patient. The parameter values include an insulin action speed and a target glucose value. A control module coupled to the actuation arrangement and the data storage element to receive a user input indicative of a desire to administer a bolus and, in response to the user input, determine a current insulin on board in the body of the patient based at least in part on the historical bolus data and the insulin action speed, determine a bolus delivery amount of the insulin based at least in part on the current insulin on board and the target glucose value, and configure the actuation arrangement to automatically deliver the bolus delivery amount of the insulin from the container in response to manual actuation of the delivery button.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Embodiments of the subject matter described herein generally relate to fluid injection devices, such as injection pens, that are utilized to manually administer correction boluses at an injection site as desired by a user (e.g., on-demand). In response to a user manipulating an injection pen to initiate a new bolus, the injection pen automatically calculates or otherwise determines a corresponding fluid delivery amount for the new bolus using historical bolus data pertaining to previously-administered boluses and one or more patient-specific parameter values stored onboard the injection pen. When the determined bolus delivery amount is accepted or confirmed by the user, the injection pen automatically configures its actuation arrangement so that the determined bolus amount is automatically delivered by the injection pen to the body of the patient in response to manual actuation of a user interface element of the injection pen. In this manner, the bolus delivery amount may be accurately and reliably determined by the injection pen in a patient-specific manner, and the resulting determined amount of fluid is precisely delivered in an automated manner that reduces the workload on the user and reduces the likelihood of human error.

Figure 1:
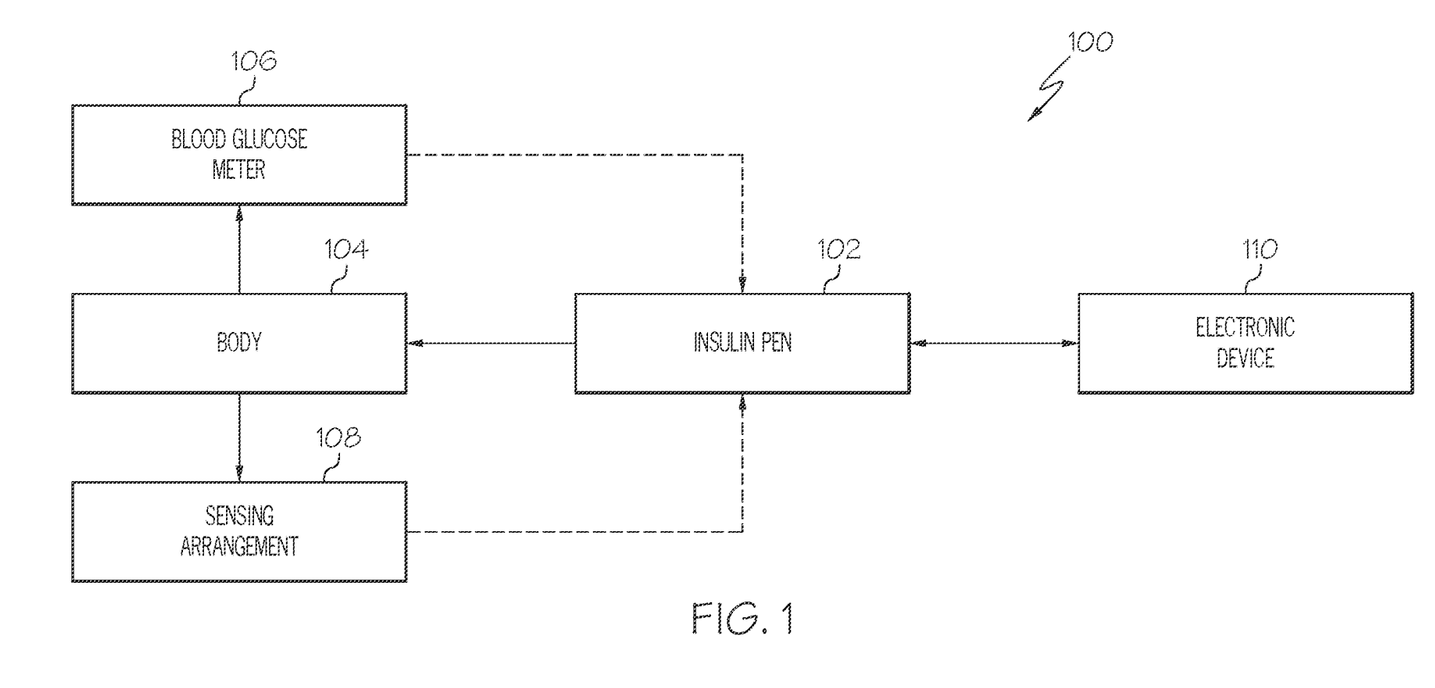
FIG. 1 depicts an exemplary embodiment of an injection system.

FIG. 1 depicts an exemplary embodiment of an injection system 100 that includes a fluid injection pen 102 used to administer boluses of fluid to the body 104 of a patient in an on-demand or as needed basis to regulate a physiological condition of the patient that is influenced by the fluid. In exemplary embodiments described herein, the fluid injection pen 102 is utilized to administer boluses of insulin to regulate a glucose level in the body 104 of the patient. However, it should be appreciated that many other fluids may be administered through infusion such as, but not limited to, HIV drugs, drugs to treat pulmonary hypertension, iron chelation drugs, pain medications, anti-cancer treatments, medications, vitamins, hormones, nutritional supplements, dyes, a tracing medium, a saline medium, a hydration medium, or the like. That said, for purposes of explanation, but without limitation, the subject matter is described herein in the context of an insulin injection pen for administering boluses of insulin.

The illustrated injection system 100 includes one or more measurement devices 106, 108 for obtaining measurement values for the physiological condition in the body 104 of the patient that is being regulated. For example, an insulin injection system 100 may include a blood glucose meter 106, such as a finger stick device, capable of directly sensing, detecting, measuring or otherwise quantifying the blood glucose level in the body 104 of the user. In one or more exemplary embodiments, the insulin pen 102 receives or otherwise obtains a current (or most recent) blood glucose measurement value measured by the blood glucose meter 106 and calculates or otherwise determines a bolus delivery amount for operating the insulin pen based at least in part on the current blood glucose measurement value. Depending on the embodiment, blood glucose measurement values obtained via the blood glucose meter 106 may be manually input to the insulin pen 102 by a user, or the insulin pen 102 may be communicatively coupled to the blood glucose meter 106 to receive blood glucose measurement values from the blood glucose meter 106 directly.

In various embodiments, the insulin injection system 100 additionally or alternatively includes a glucose sensing arrangement 108 that includes one or more interstitial glucose sensing elements that generate or otherwise output electrical signals having a signal characteristic that is correlative to, influenced by, or otherwise indicative of the relative interstitial fluid glucose level in the body 104 of the patient. In this regard, the sensing arrangement 108 may be secured to the body 104 of the patient or embedded in the body 104 of the patient as part of a continuous glucose monitoring system. The sensed interstitial fluid glucose values obtained by the sensing arrangement 108 may be converted into corresponding blood glucose values using one or more calibration factors, which may be determined, for example, using one or more reference blood glucose measurement values obtained via the blood glucose meter 106. In one or more embodiments, the insulin pen 102 receives or otherwise obtains one or more sensed glucose measurement values from the sensing arrangement 108 and calculates or otherwise determines a bolus amount in a manner that is influenced by the sensed glucose measurement value(s). In this regard, sensed glucose measurement values from the sensing arrangement 108 may be used in addition to or in alternative to blood glucose measurement values from the blood glucose meter 106. In such embodiments, the insulin pen 102 may be communicatively coupled to the sensing arrangement 108 to receive the sensed glucose measurement values from the sensing arrangement 108 directly in a substantially continuous manner when the injection pen 102 is turned on or otherwise enabled and within range of the sensing arrangement 108.

As described in greater detail below in the context of FIGS. 2-3, in exemplary embodiments, the injection pen 102 stores or otherwise maintains patient-specific values for various control parameters utilized to determine the bolus amount for delivery to the patient. Depending on the embodiment, the patient-specific values may be manually input to the injection pen 102 by a user (e.g., using user interface elements of the injection pen 102), or alternatively, the patient-specific values may be received by the injection pen 102 from another electronic device 110, such as a desktop computer, a cell phone or other mobile telephone, a laptop or notebook computer, a tablet computer, a personal digital assistant, a remote server, and/or any other suitable computing device. For example, the injection pen 102 may be communicatively coupled to the electronic device 110 via a communications network (e.g., the Internet, a wireless local area network (WLAN), a Bluetooth network, a cellular network, or the like). A user of the electronic device 110 may download (e.g., from a remote server via a communications network) or otherwise install a client application on the electronic device 110 that facilitates communications between the electronic device 110 and the injection pen 102. The client application may generate or otherwise provide a graphical user interface on the electronic device 110 that includes graphical user interface elements (e.g., text boxes, drop-down menus, buttons, and the like) that may be manipulated by a user to manually input the patient-specific parameter values and transmit the patient-specific parameter values to the injection pen 102.

In practice, the patient (or another user) enables, turns on, or otherwise manipulates the injection pen 102 to deliver a bolus of fluid to the patient's body 104 as desired throughout the day. For example, at meal time, the patient may utilize the blood glucose meter 106 to obtain a current glucose measurement value, and then turn on the injection pen 102 to initiate a meal bolus. In such embodiments, a user inputs or otherwise provides an amount of carbohydrates associated with the meal. For example, the patient may manipulate user interface elements associated with the injection pen 102 to input the carbohydrate amount directly to the injection pen 102, or alternatively, that patient may manipulate the electronic device 110 to receive and then transfer, to the injection pen 102, a carbohydrate amount that is input to the client application on the electronic device 110. Additionally, in embodiments where the injection pen 102 does not communicate with the blood glucose meter 106, the patient may input the current glucose measurement value to the injection pen 102 (either directly or via the electronic device 110). Based at least in part on the input carbohydrate amount, the current glucose measurement value, and the stored patient-specific parameter values, the injection pen 102 automatically calculates or otherwise determines a meal bolus amount configured to compensate for the carbohydrates in a patient-specific manner.

When the bolus amount determined by the injection pen 102 is confirmed or otherwise accepted by a user, the injection pen 102 automatically configures its actuation arrangement to precisely deliver the bolus amount automatically in response to manual actuation of a user interface element of the injection pen 102 (e.g., a button associated with fluid delivery). For example, a motor command corresponding to the bolus amount may be automatically determined and provided to a motor control module for subsequent execution in response to manual actuation of a delivery button. In other embodiments, the injection pen 102 may include an autoinjection mechanism that is configurable, programmable, or otherwise adjustable to automatically deliver the determined bolus amount in response to manual actuation of the delivery button. For example, the autoinjection mechanism may be realized as a spring-loaded delivery mechanism that is configured to automatically displace a plunger within a reservoir, cartridge, or other fluid container associated with the injection pen 102 by a particular distance upon actuation of a delivery button on the injection pen, where that distance (or amount of displacement) is adjustable by a control module or the injection pen 102 (e.g., by varying a physical feature or component that restricts the compression or extension of the spring-loading) to deliver the precise bolus amount that is calculated or otherwise determined by the injection pen 102. Alternatively, the position, orientation, or other characteristic of a physical feature or element of the injection pen 102 that controls, regulates, restricts or otherwise limits delivery (e.g., by limiting the range of motion or displacement of the motor, a slide or plunger, or some other component of the actuation arrangement) may be automatically adjusted to allow the actuation arrangement to deliver the determined bolus amount in response to manual actuation of the delivery button.

Figure 2:
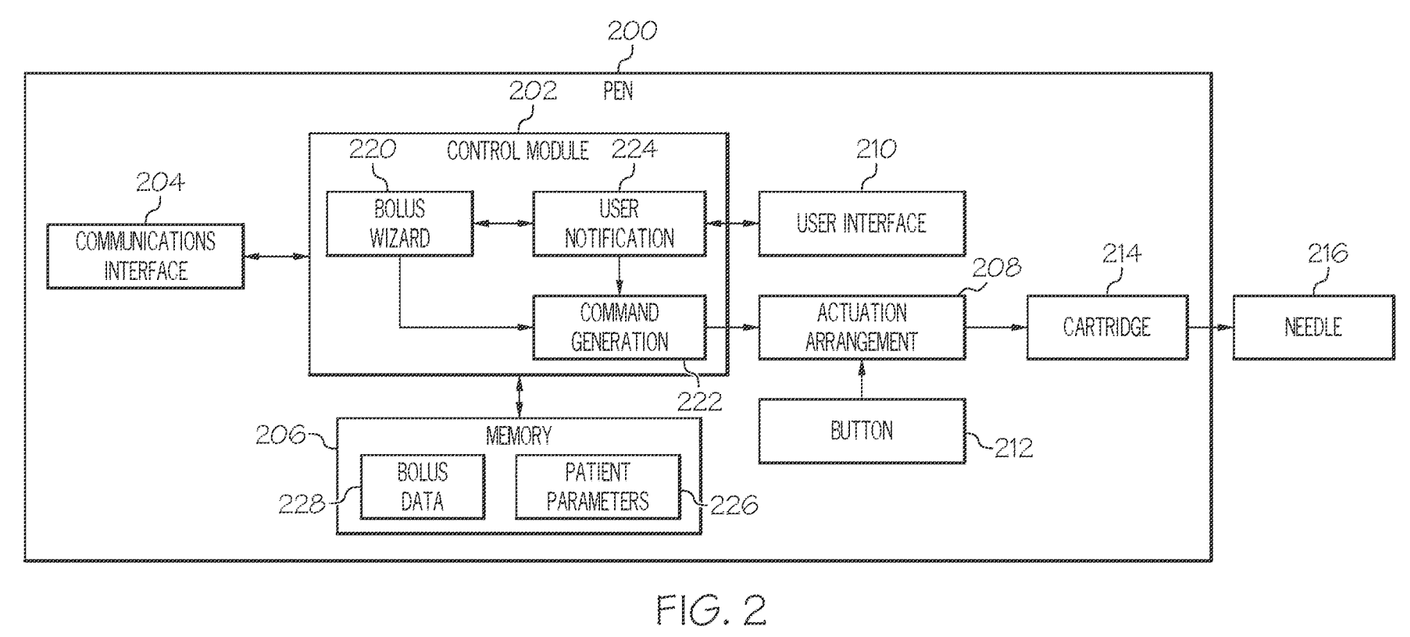
FIG. 2 depicts a block diagram of an exemplary embodiment of an injection pen suitable for use in the injection system of FIG. 1.

FIG. 2 depicts an exemplary embodiment of an injection pen 200 suitable for use as the injection pen 102 in the injection system 100 of FIG. 1 in accordance with one or more embodiments. The illustrated injection pen 200 includes, without limitation, a pen control module 202, a communications interface 204, a data storage element (or memory) 206, an actuation arrangement 208, and user interface elements 210, 212. The pen control module 202 is coupled to the communications interface 204, the memory 206, the actuation arrangement 208, and the user interface elements 210, 212, and the pen control module 202 is suitably configured to support the operations, tasks, and/or processes described herein. In this regard, the pen control module 202 supports operation of the actuation arrangement 208 in response to manual actuation of a user interface element 212 to deliver a particular bolus amount of fluid from a fluid container 214 (e.g., a cartridge or reservoir) to an injection site in the body 104 of a patient via a needle 216.

The communications interface 204 generally represents the hardware, circuitry, logic, firmware and/or other components of the injection pen 200 that are coupled to the pen control module 202 and configured to support communications between the injection pen 200 and one or more external electronic devices of an injection system 100 (e.g., the blood glucose meter 106, the glucose sensing arrangement 108, and/or the electronic device 110). In exemplary embodiments, the communications interface 204 includes or is otherwise coupled to one or more transceiver modules capable of supporting wireless communications; however, in some embodiments, the communications interface 204 may be configured to support wired communications.

The user interface element(s) 210 generally represents the hardware, circuitry, logic, firmware and/or other components of the injection pen 200 configured to support user interactions between the pen control module 202 and a patient or user. The one or more user interface element(s) 210 associated with the injection pen 200 may include at least one input user interface element, such as, for example, a button, a keypad, a knob, a touch panel, a touchscreen, and/or the like. Additionally, the one or more user interface element(s) 210 may include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. In the illustrated embodiment, user interface element 212 represents an input user interface element of the injection pen 200 that is actuatable by a user to produce corresponding operation of the actuation arrangement 208 to deliver a bolus of fluid from the fluid container 214 via the needle 216. In one or more embodiments, the input user interface element 212 is realized as a tactile depressible button that is associated with the delivery of a bolus from the injection pen 200, and accordingly, the input user interface element 212 may alternatively be referred to herein, without limitation, as a delivery button.

The pen control module 202 generally represents the hardware, circuitry, logic, firmware and/or other component(s) of the injection pen 200 that is configured to determine bolus dosage commands for configuring or otherwise operating the actuation arrangement 208 to deliver fluid from the fluid container 214 and perform various additional tasks, operations, functions and/or operations described herein. Depending on the embodiment, the pen control module 202 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pen control module 202, or in any practical combination thereof.

In exemplary embodiments, the pen control module 202 includes or otherwise accesses the data storage element or memory 206, which may be realized using any sort of non-transitory computer-readable medium capable of storing programming instructions for execution by the pen control module 202. The computer-executable programming instructions, when read and executed by the pen control module 202, cause the pen control module 202 to perform the tasks, operations, functions, and processes described herein. In this regard, a control scheme or algorithm implemented by the pen control module 202 may be realized as control application code that is stored or otherwise maintained in the memory 206 and executed by the pen control module 202 to implement or otherwise provide one or more of the components in software. For example, the control application code may be executed by the control module 202 to generate a bolus wizard application 220 that calculates or otherwise determines the amount of fluid to be bolused to a patient, as described in greater detail below in the context of FIG. 3. Similarly, the pen control module 202 may also implement or otherwise execute a command generation application 222 that converts a bolus amount from the bolus wizard application 220 into a corresponding command for operating or otherwise configuring the actuation arrangement 208 for dispensing the bolus amount from the container 214. The illustrated pen control module 202 also implements or otherwise executes a user notification application 224 that supports interactions with the patient or other users via the user interface element(s) 210 associated with the injection pen 200, as described in greater detail below.

Still referring to FIG. 2, the parameter registers 226 generally represent the hardware, circuitry and/or other components of the injection pen 200 that are configured to store the patient-specific physiological parameters or other control information utilized by the bolus wizard application 220 of the pen control module 202 in determining a bolus amount in a patient-specific manner. For example, the parameter registers 226 may store or otherwise maintain one or more patient-specific insulin sensitivity factor values, carbohydrate-to-insulin ratio values, insulin action speed values, target glucose values, and the like. The patient-specific insulin sensitivity factor value reflects the patient's sensitivity to insulin (e.g., an amount of drop in glucose level per unit of insulin administered). In practice, multiple different patient-specific insulin sensitivity factor values may be input by a user and stored by the injection pen 200 in association with particular time periods to support subdividing the day into multiple segments that reflect or otherwise account for diurnal variations in the patient's insulin sensitivity. The carbohydrate-to-insulin ratio value defines how many grams of carbohydrates one unit of insulin can compensate for, and similarly, multiple different carbohydrate-to-insulin ratio values may be input by a user and stored by the injection pen 200 in association with particular time periods to account for diurnal variations exhibited by the patient. The insulin action speed value represents the amount of time insulin remains active in the patient's body (e.g., the amount of time required to clear a unit of insulin).

In exemplary embodiments, the parameter registers 226 are capable of storing or otherwise maintaining a low target glucose value ($T_L$) and a high target glucose value ($T_H$), which are utilized when calculating the bolus amount. In this regard, the high target glucose value ($T_H$) is the desired glucose level that the user would like to achieve or stay below after delivering a bolus, and the low target glucose value ($T_L$) is the desired glucose level that the user would like to achieve or stay above after delivering a bolus. Again, multiple different sets of target glucose values may be input by a user and stored by the injection pen 200 in association with particular time periods to support subdividing the day into multiple segments.

In exemplary embodiments, the memory 206 also includes registers 228 (or other allocation) configured to store historical bolus data for the injection pen 200. In this regard, the bolus data portion 228 of memory 206 stores or otherwise maintains information identifying the respective amounts of previous boluses and the respective delivery times associated with those previous boluses. As described in greater detail below in the context of FIG. 3, the historical bolus data for the injection pen 200 is utilized to calculate, estimate, or otherwise determine the amount of active insulin on-board (IOB) in the body 104 of the patient using the patient-specific insulin action speed value.

In the embodiment of FIG. 2, the actuation arrangement 208 generally represents the hardware, circuitry and/or other electrical, mechanical, or electromechanical components of the injection pen 200 that are configured to enable or otherwise facilitate delivering boluses of fluid from the fluid container 214 to the patient's body 104 via the needle 216. For example, the actuation arrangement 208 may include a motor mechanically coupled to a drive train assembly configured to translate rotational motor motion into linear displacement of a slide, shaft, or the like that produces a corresponding displacement of a plunger or stopper within the fluid container 214 towards the needle 216. In an alternative embodiment, the actuation arrangement 208 includes adjustable or configurable drive train components that are configured to selectively restrict or otherwise limit the range of motion (or amount of displacement) of the plunger or stopper within the fluid container 214, and thereby limit the amount of fluid that may be dispensed from the injection pen 200 when an actuatable user interface element 212 of the injection pen 200 (e.g., a depressible delivery button) is manually manipulated.

It should be understood that FIG. 2 is a simplified representation of the injection pen 200 for purposes of explanation and is not intended to limit the subject matter described herein in any way. In this regard, although FIG. 2 depicts the user interface elements 210, 212 as being integrated with the injection pen 200, in various alternative embodiments, one or more of the user interface element 210, 212 may be integrated with another device in the injection system 100 that is communicatively coupled to the injection pen 200 (e.g., the electronic device 110). Furthermore, although FIG. 2 depicts the fluid container 214 being onboard the injection pen 200, it will be appreciated that the container 214 may be physically separate from the injection pen 200 and detachable, removable or otherwise replaceable upon depletion. Similarly, although FIG. 2 depicts the needle 216 as being separate from the injection pen 200 (e.g., a detachable or replaceable needle), in some embodiments, the needle 216 may be integrated or otherwise fixedly engaged with the housing of the injection pen 200. Additionally, while FIG. 2 depicts registers 226, 228 as being integrated with or into the memory 206, in various embodiments, either or both of the registers 226, 228 may be distinct or otherwise separate from memory 206, and the registers 226, 228 may be integrated with the pen control module 202 or with one another separate from the memory 206.

Figure 3:
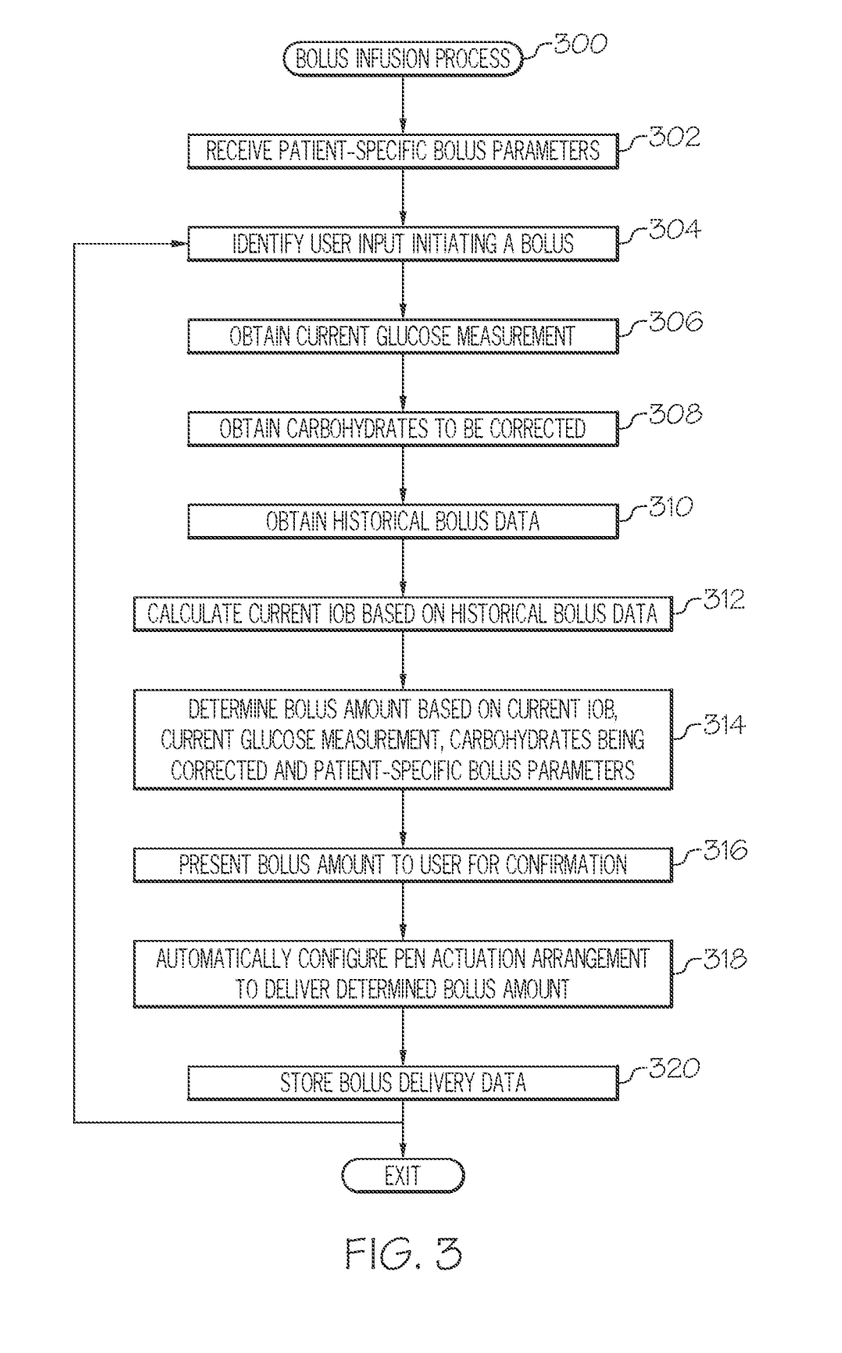
FIG. 3 is a flow diagram of an exemplary bolus infusion process suitable for use with the insulin pen of FIG. 2 in the injection system of FIG. 1.

FIG. 3 depicts an exemplary bolus infusion process 300 suitable for use with the injection pen 102, 200 in the injection system 100 to deliver boluses to the body 104 of a patient. Various tasks performed in connection with the bolus infusion process 300 may be performed by hardware, firmware, software executed by processing circuitry, or any combination thereof. For illustrative purposes, the following description refers to elements mentioned above in connection with FIGS. 1-2. In practice, portions of the bolus infusion process 300 may be performed by different elements of the injection system 100, such as, for example, injection pen 102, 200, the pen control module 202, the blood glucose meter 106, the glucose sensing arrangement 108, the electronic device 110, the communications interface 204, the actuation arrangement 208, and/or the user interface elements 210, 212. It should be appreciated that the bolus infusion process 300 may include any number of additional or alternative tasks, the tasks need not be performed in the illustrated order and/or the tasks may be performed concurrently, and/or the bolus infusion process 300 may be incorporated into a more comprehensive procedure or process having additional functionality not described in detail herein. Moreover, one or more of the tasks shown and described in the context of FIG. 3 could be omitted from a practical embodiment of the bolus infusion process 300 as long as the intended overall functionality remains intact.

Referring to FIG. 3 with continued reference to FIGS. 1-2, the illustrated bolus infusion process 300 receives or otherwise obtains patient-specific bolus parameters (task 302). Upon initial deployment of the injection pen 102, 200, a user may manipulate user interface elements 210 on the injection pen 102, 200 to associate or otherwise configure the injection pen 102, 200 for use with a particular patient (i.e., the person whose body 104 will receive the administered boluses from the injection pen 102, 200). For example, a user may manipulate user interface elements 210 on the injection pen 102, 200 to manually input or otherwise provide values for physiological parameters or other bolus control information which are specific to the particular patient that will be associated with the injection pen 102, 200. In other embodiments, a user may utilize an application on a client electronic device 110 to input or otherwise provide patient-specific values that are transmitted or otherwise provided to the injection pen 102, 200 and received via the communications interface 204. In yet other embodiments, a user may manipulate user interface elements 210 on the injection pen 102, 200 to input or otherwise provide a unique identifier associated with the patient, which, in turn, is utilized by the injection pen 102, 200 to download patient-specific values associated with that unique identifier from a remote server 110. As described above, the patient-specific values received for the physiological parameters or other bolus control information are stored or otherwise maintained by the memory 206 and/or the patient-specific parameter registers 226 of the injection pen 102, 200.

After the injection pen is configured for use with a particular patient, the bolus infusion process 300 receives, detects, or otherwise identifies a user input indicative of a desire to administer a bolus (task 304). In this regard, at various times during the day, the patient or other user may determine that it is desirable to administer a bolus, and accordingly manipulate a user interface element 210, 212 associated with the injection pen 102, 200 to initiate self-administration of a bolus from the injection pen 102, 200. In one embodiment, the pen control module 202 and/or the bolus wizard application 220 detects or otherwise identifies a user manipulating a user interface element 210, 212 to power on, wake, or otherwise activate the injection pen 102, 200 as indicating a desire to administer a bolus.

In response to identifying a user input indicative of a desire to administer a bolus, the illustrated bolus infusion process 300 receives or otherwise obtains a current glucose measurement for the patient (task 306). In this regard, the current (or most recent) glucose measurement represents the state of the physiological condition of the patient substantially contemporaneously with the bolus to be delivered. In some embodiments, the patient or other user may manipulate one or more user interface elements 210 associated with the injection pen 102, 200 to manually input or otherwise provide the current blood glucose measurement value most recently obtained via the blood glucose meter 106 to the pen control module 202. In other embodiments, a user may read the measurement value output by the blood glucose meter 106 and utilize an application on a client electronic device 110 to input or otherwise provide the most recent measurement value from the blood glucose meter 106, which is then transmitted or otherwise provided to the injection pen 102, 200. In yet other embodiments, in response to detecting a desire to administer a bolus, the pen control module 202 may interact with the communications interface 204 to automatically transmit a request for the current (or most recent) measurement data from the blood glucose meter 106 and/or the sensing arrangement 108. For example, the communications interface 204 may scan or otherwise detect which measurement devices 106, 108 are within communications range of the injection pen 102, 200 and provide indication of the available measurement device(s) 106, 108 to the pen control module 202, which, in turn, automatically requests the most recent glucose measurement value from a particular measurement device 106, 108 as desired. When the bolus wizard application 220 receives an interstitial glucose measurement value from the sensing arrangement 108, the bolus wizard application 220 utilizes a previously-determined calibration factor to convert the interstitial glucose measurement value into a corresponding blood glucose value.

In some embodiments, the bolus wizard application 220 may average or otherwise combine the glucose measurement values obtained from multiple measurement devices 106, 108 within an injection system 100 to arrive at a current glucose measurement value corresponding to the delivery time (or current time) for the bolus to be delivered. For example, the bolus wizard application 220 may identify or otherwise determine a trend in interstitial glucose measurement values from the sensing arrangement 108 and adjust the most recent blood glucose measurement value from the blood glucose meter 106 to obtain an adjusted blood glucose measurement value used for determining the bolus delivery amount.

When the bolus is intended to compensate for carbohydrates consumed by the patient, the bolus infusion process 300 also receives or otherwise obtains an amount of carbohydrates to be corrected for by the bolus (task 308). For example, the patient or other user may manipulate one or more user interface elements 210 associated with the injection pen 102, 200 to indicate the bolus is a meal bolus, and then manually input or otherwise provide the amount of carbohydrates to be compensated for in a similar manner as described above. In other embodiments, the type and/or amount of food may be identified, which, in turn, is converted from a particular amount of a particular type of food into a corresponding carbohydrate amount by the bolus wizard application 220 using a food lookup table or the like. As described above, a user may also utilize an application on a client electronic device 110 to input or otherwise provide the amount of carbohydrates to be corrected, which is then transmitted or otherwise provided to the injection pen 102, 200.

Still referring to FIG. 3, the bolus infusion process 300 continues by retrieving or otherwise obtaining historical bolus delivery data for the patient and calculating, estimating, or otherwise determining a current amount of insulin on board for the patient based at least in part on the historical bolus delivery data and one or more of the patient-specific parameter values (tasks 310, 312). In exemplary embodiments, each time the injection pen 102, 200 delivers a bolus to the patient, the control module 202 and/or the bolus wizard application 220 stores or otherwise maintains, in the historical bolus data portion 228 of the memory 206, information identifying the amount of insulin delivered and a delivery time associated with the delivery (e.g., the current time contemporaneous to the bolus delivery). Using the insulin delivery amount for each previously-delivered bolus, the corresponding delivery time associated with each respective previously-delivered bolus, and the patient-specific insulin action speed value, the bolus wizard application 220 calculates or otherwise determines a current insulin on board for the patient at the current time for the bolus to be delivered.

In one exemplary embodiment, the bolus wizard application 220 recursively calculates the current insulin on board. For example, the amount of insulin on board at a particular sampling time ($IOB_N$) may be represented by the equation:

$$IOB_N = Ic_{N-1}IOB_{N-1} + Ic_{N-2}IOB_{N-2} + Ic_{N-3}IOB_{N-3} + Bc_{N-1}B_{N-1} + Bc_{N-2}B_{N-2} + Bc_{N-3}B_{N-3},$$

where Ic represents insulin on board compensation coefficients associated with the respective insulin on board amounts at respective preceding sampling times, Bc represents bolus compensation coefficients associated with the respective bolus delivery amounts ($B_N$) at respective preceding sampling times. The insulin on board and bolus compensation coefficients are calculated using the following equations:

$$IC_{N-1} = eaxx1 + eaxx2 + eaxx3;$$

$$IC_{N-2} = (eaxx1\,eaxx2 + (eaxx1 + eaxx2)eaxx3);$$

$$I_{CN-3} = eaxx1\,eaxx2\,eaxx3;$$

$$Bc_{N-1} = 1;$$

$$BC_{N-2} = d\mathrm{prod}(-(daxx21\,eaxx1 + daxx21\,eaxx2)\\
axx1\,axx2 + (daxx31\,eaxx1 + daxx31\,eaxx3)\\
axx1\,axx3 - (daxx32\,eaxx2 + daxx32\,eaxx3)\\
axx2\,axx3);\ \text{and}$$

$$BC_{N-3} = d\mathrm{prod}(daxx21\,eaxx1\,eaxx2\,axx1\,axx2 +\\
daxx32\,eaxx2\,eaxx3\,axx2\,axx3 -\\
daxx31\,eaxx1\,eaxx3\,axx1\,axx3).$$

The intermediate variables of the insulin on board and bolus compensation coefficients are calculated based on the sampling time interval (Ts), the patient-specific insulin action speed value (Csp), a time constant associated with the subcutaneous compartment (IFBTFast), a time constant associated with the plasma compartment (IFBTSlow), and a time constant associated with the interstitial compartment (IFBTEffect), using the following equations:

$$axx1 = 1/\mathrm{IFBTFast};$$

$$axx2 = 1/\mathrm{IFBTSlow};$$

$$axx3 = 1/\mathrm{IFBTEffect};$$

$$dtC = 6Ts/Csp;$$

$$eaxx1 = \exp(-axx1\,dtC);$$

$$eaxx2 = \exp(-axx2\,dtC);$$

$$eaxx3 = \exp(-axx3\,dtC);$$

$$daxx21 = axx2 - axx1;$$

$$daxx31 = axx3 - axx1;$$

$$daxx32 = axx3 - axx2;\ \text{and}$$

$$d\mathrm{prod} = 1/(daxx21\,daxx31\,daxx32).$$

To obtain the current insulin on board ($IOB_N$), in exemplary embodiments, the bolus wizard application 220 recursively calculates the current insulin on board starting from the most recent delivery time associated with the preceding insulin bolus delivered by the injection pen 102, 200 (i.e., by determining an initial insulin on board at the most recent delivery time) and incrementally toward the current time at the sampling time interval (Ts). In this regard, in addition to storing the insulin delivery amount ($B_{N-x}$) for a previously-delivered bolus, the bolus wizard application 220 may also store or otherwise maintain the calculated insulin on board at that corresponding delivery time ($IOB_{N\text{-}x}$) along with the preceding insulin on board amounts (e.g., $IOB_{N\text{-}(x-1)}$ and $IOB_{N\text{-}(x-2)}$). In this regard, after initializing the current insulin on board equation at the preceding bolus delivery time, for each subsequent iteration, the current insulin on board equation is incrementally updated for the next incremental sampling time after the previous bolus delivery time by setting $IOB_{N-3} = IOB_{N-2}$, $IOB_{N-2} = IOB_{N-1}$, $IOB_{N-1} = IOB_N$, $B_{N-3} = B_{N-2}$, $B_{N-2} = B_{N-1}$, and $B_{N-1} = 0$ (assuming no bolus delivery since the most recent bolus data stored in the memory 206, 228). It should be noted that in some embodiments, the values for the sampling time interval (Ts), the time constant associated with the subcutaneous compartment (IFBTFast), the time constant associated with the plasma compartment (IFBTSlow), and/or the time constant associated with the interstitial compartment (IFBTEffect) may be patient-specific or otherwise user-configurable and stored in the patient parameter registers 226.

After determining the current insulin on board, the bolus infusion process 300 calculates or otherwise determines a fluid delivery amount for the bolus based on the current insulin on board, the current glucose measurement value, the amount of carbohydrates being corrected (in the case of a meal bolus), and one or more of the patient-specific bolus parameter values (task 314). In exemplary embodiments, in the case of a correction bolus (e.g., the amount of carbohydrates being corrected is equal to zero), the bolus wizard application 220 calculates or otherwise determines the bolus delivery amount based on the difference between the current glucose measurement value and the patient-specific high target glucose value ($T_H$). In this regard, when the current glucose measurement value is less than the high target glucose value, the bolus wizard application 220 determines the bolus delivery amount is equal to zero. Conversely, when the current glucose measurement value is greater than the high target glucose value, the bolus wizard application 220 determines the correction bolus delivery amount (CB) based on the difference between the current glucose measurement value (BG) and the high target glucose value in a manner that accounts for the current insulin on board (IOB) and the patient-specific insulin sensitivity factor value (ISF) for the current time of day using the equation:

$$CB = \frac{BG - T_H}{ISF} - IOB.$$

In exemplary embodiments, the case of a meal bolus, the bolus wizard application 220 calculates or otherwise determines the bolus delivery amount based on the relationship between the current glucose measurement value and the patient-specific high and low target glucose values. In this regard, when the current glucose measurement value (BG) is greater than the high target glucose value ($T_H$), the bolus wizard application 220 determines the meal bolus delivery amount (MB) intended to result in a future glucose level that is less than the high target glucose value based on the amount of carbohydrates being corrected (Carb) using the equation:

$$MB = \frac{Carb}{CR} + CB,$$

where CR represents the patient-specific carbohydrate-to-insulin ratio applicable for the current time of day, and $$CB = \frac{BG - T_H}{ISF} - IOB,$$

as described above. Conversely, when the current glucose measurement value (BG) is less than the low target glucose value ($T_L$), the bolus wizard application 220 determines the meal bolus delivery amount intended to result in a future glucose level that is greater than the low target glucose value using the equation:

$$MB = \frac{Carb}{CR} + \frac{BG - T_L}{ISF},$$

where ISF represents the patient-specific insulin sensitivity factor applicable for the current time of day. In the event a current glucose measurement value is unavailable, the bolus wizard application 220 may determine the meal bolus delivery amount based on the ratio of the amount of carbohydrates being corrected to the patient-specific carbohydrate-to-insulin ratio (e.g., $$MB = \frac{Carb}{CR}$$

In the illustrated embodiment, the bolus infusion process 300 displays or otherwise presents the determined bolus delivery amount to a user for verification or confirmation (task 316). In this regard, if one of the user interface elements 210 of the injection pen 102, 200 is realized as a display device, the pen control module 202 generates or otherwise provides a graphical representation of the correction bolus delivery amount or meal bolus delivery amount determined by the bolus wizard application 220 on the display device 210. In some embodiments, the pen control module 202 also generates or otherwise provides a graphical user interface element on the display device 210 that may be manipulated by the user to verify or otherwise confirm the bolus delivery amount should be administered. In other embodiments, another user interface element 210, 212 of the injection pen 102, 200 may be manipulated to indicate confirmation of the bolus delivery amount for delivery. In other embodiments, the pen control module 202 may transmit or otherwise provide the determined bolus delivery amount from the bolus wizard application 220 to the electronic device 110, which, in turn, generates or otherwise provides a graphical representation of the determined bolus delivery amount and includes graphical user interface elements and/or physical user interface elements of the electronic device 110 that may be manipulated by the user to verify or otherwise confirm the bolus delivery amount should be administered. In some embodiments, when the patient or user is unsatisfied with the bolus delivery amount, the user interface elements 210 associated with the injection pen 102, 200 and/or the electronic device 110 may be manipulated to manually adjust the bolus delivery amount.

In response to confirmation of the determined bolus delivery amount, the bolus infusion process 300 configures the injection pen to automatically deliver the determined bolus delivery amount (task 318). For example, in one embodiment, the bolus delivery amount determined by the bolus wizard application 220 is provided to the command generation application 222, which, in turn, generates commands for operating the actuation arrangement 208 corresponding to the bolus delivery amount. In this regard, the command generation application 222 may convert the bolus delivery amount determined by the bolus wizard application 220 to a corresponding motor command (or sequence of motor commands) that will be executed or otherwise implemented by a motor of the actuation arrangement 208 in response to subsequent manual manipulation of the delivery button 212, so that the determined bolus delivery amount is automatically delivered independent of the characteristics of the user's actuation of the delivery button 212 (e.g., independently of the applied force and/or the duration thereof).

In alternative embodiments, where the actuation arrangement 208 includes an autoinjection mechanism, the command generation application 222 may provide appropriate commands to the actuation arrangement 208 to adjust, program, or otherwise configure one or more components of the autoinjection mechanism to automatically deliver the bolus delivery amount in response to subsequent manual actuation of the delivery button 212. Again, in such embodiments, the determined bolus delivery amount is automatically delivered independent of the physical or temporal characteristics of the user's actuation of the delivery button 212. Alternatively, in yet other embodiments, the command generation application 222 may configure an adjustable physical feature or other element of the actuation arrangement 208 (e.g., by adjusting its position, orientation, or other characteristic) to restrict or otherwise limit delivery of fluid from the cartridge 214 to the determined bolus amount in response to manual actuation of the delivery button 212. Thus, the determined bolus delivery amount may be delivered independent of the characteristics of the user's actuation of the delivery button 212 by automatically limiting the range of motion or displacement of the motor, a slide or plunger within the cartridge 214, or some other component of the actuation arrangement 208.

In response to delivery of a bolus, the bolus infusion process 300 updates the historical bolus data maintained by the injection pen to store or otherwise maintain information associated with the bolus delivery (task 320). For example, the pen control module 202 may detect or otherwise identify delivery of the bolus by detecting manual actuation of the delivery button 212 or detecting operation of the actuation arrangement 208 to deliver fluid from the cartridge 214. In response, the pen control module 202 stores or otherwise maintains, in the historical bolus data portion 228 of the memory 206, the current delivery time associated with the bolus delivery, the fluid delivery amount associated with the bolus delivery, and the current insulin on board at the current delivery time. Thereafter, during a subsequent iteration of the bolus infusion process 300 at a subsequent time, the bolus wizard application 220 utilizes the stored delivery time, the insulin delivery amount, and the insulin on board associated with the bolus delivery for calculating a current insulin on board at that subsequent time as described above (e.g., task 312). In this regard, the loop defined by tasks 304, 306, 308, 310, 312, 314, 316, 318 and 320 may repeat to dynamically determine bolus delivery amounts and automatically configure the injection pen to automatically deliver the determined bolus delivery amounts as desired.

For the sake of brevity, conventional techniques related to glucose sensing and/or monitoring, glucose control, correction boluses, meal boluses, sensor calibration and/or compensation, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A non-transitory computer-readable medium comprising executable instructions that, when read and executed by a processor, cause the processor to:
receive user input indicative of a desire to administer a bolus;
receive, via a communications network, one or more measurement values from a sensing arrangement including one or more interstitial sensing elements;
determine an adjusted measurement value corresponding to a time for the bolus to be delivered in response to receiving the user input indicative of the desire to administer the bolus based at least in part on the one or more measurement values;
recursively determine an active amount of fluid in a body of a patient at the time for the bolus to be delivered based at least in part on historical bolus data associated with previous boluses delivered to the patient, by iteratively determining a plurality of intermediate values of active amount of fluid in the body of the patient associated with a plurality of intermediate times between (a) a most recent fluid delivery time and (b) the time for the bolus to be delivered, wherein each of the plurality of intermediate values of active amount of fluid in the body is determined for a particular intermediate time, from the plurality of intermediate times, that occurs after the most recent fluid delivery time and before the time for the bolus to be delivered; and
determine a bolus delivery amount of the fluid based at least in part on the active amount of the fluid and a difference between the adjusted measurement value and a target value.

2. The computer-readable medium of claim 1, wherein the instructions cause the processor to determine a bolus dosage command for configuring a fluid injection device to deliver the bolus delivery amount.

3. The computer-readable medium of claim 2, wherein the instructions cause the processor to transmit the bolus dosage command to the fluid injection device via the communications network.

4. The computer-readable medium of claim 1, wherein the instructions cause the processor to generate a graphical user interface for a client application that includes a graphical user interface element that may be manipulated by a user to confirm the bolus delivery amount.

5. The computer-readable medium of claim 1, wherein the instructions cause the processor to generate a graphical user interface for a client application that includes a graphical user interface element that may be manipulated by a user to adjust the bolus delivery amount.

6. The computer-readable medium of claim 1, wherein the instructions cause the processor to generate a graphical user interface for a client application that includes a graphical user interface element that may be manipulated by a user to manually input a patient-specific parameter value and recursively determine the active amount of fluid in the body of the patient at the time for the bolus to be delivered based at least in part on the historical bolus data associated with previous boluses delivered to the patient using the patient-specific parameter value.

7. The computer-readable medium of claim 1, wherein the instructions cause the processor to generate a graphical user interface for a client application that includes a graphical user interface element that may be manipulated by a user to manually input a patient-specific parameter value and determine the bolus delivery amount of the fluid based at least in part on the active amount of the fluid and the difference between the adjusted measurement value and the target value using the patient-specific parameter value.

8. The computer-readable medium of claim 1, wherein the one or more measurement values comprise one or more interstitial glucose measurement values from an interstitial glucose sensing arrangement including the one or more interstitial sensing elements.

9. The computer-readable medium of claim 8, wherein the fluid comprises insulin.

10. The computer-readable medium of claim 9, wherein the adjusted measurement value comprises an adjusted glucose measurement value and the target value comprises a target glucose value.

11. The computer-readable medium of claim 1, wherein the historical bolus data includes insulin delivery amounts for boluses previously delivered and respective delivery times associated with the respective insulin delivery amounts, wherein the instructions cause the processor to recursively determine the active amount by iteratively calculating a current insulin on board at the time associated with the user input based on the respective insulin delivery amounts, the respective delivery times, and an insulin action speed associated with the patient, wherein the insulin action speed represents an amount of time required to clear a unit of insulin from the body of the patient.

12. The computer-readable medium of claim 1, wherein the instructions cause the processor to determine a trend in the one or more measurement values and determine the adjusted measurement value in a manner that is influenced by the trend in the one or more measurement values.

13. The computer-readable medium of claim 1, wherein the instructions cause the processor to determine a correction bolus delivery amount (CB) using the equation $$CB = \frac{BG - T_H}{ISF} - IOB$$

when the adjusted measurement value (BG) is greater than a high target glucose value ($T_H$), where IOB represents the active amount of the fluid and ISF is a patient-specific insulin sensitivity factor.

14. The computer-readable medium of claim 1, wherein the instructions cause the processor to determine a meal bolus delivery amount (MB) using the equation $$MB = \frac{Carb}{CR} + \frac{BG - T_L}{ISF}$$

when the adjusted measurement value (BG) is less than a low target value ($T_L$), where Carb is an amount of carbohydrates being corrected, CR is a patient-specific carbohydrate-to-insulin ratio, and ISF is a patient-specific insulin sensitivity factor.

15. An injection system comprising:
a fluid injection device; and
a client application on an electronic device coupled to a communications network to receive user input indicative of a desire to administer a bolus, receive, via the communications network, one or more measurement values from a sensing arrangement including one or more interstitial sensing elements, determine an adjusted measurement value corresponding to a time for the bolus to be delivered in response to receiving the user input indicative of the desire to administer the bolus based at least in part on the one or more measurement values, recursively determine an active amount of fluid in a body of a patient at the time for the bolus to be delivered based at least in part on historical bolus data associated with previous boluses delivered to the patient, by iteratively determining a plurality of intermediate values of active amount of fluid in the body of the patient associated with a plurality of intermediate times between (a) a most recent fluid delivery time and (b) the time for the bolus to be delivered, wherein each of the plurality of intermediate values of active amount of fluid in the body is determined for a particular intermediate time, from the plurality of intermediate times, that occurs after the most recent fluid delivery time and before the time for the bolus to be delivered, and determine a bolus delivery amount of the fluid to be delivered by the fluid injection device based at least in part on the active amount of the fluid and a difference between the adjusted measurement value and a target value.

16. The injection system of claim 15, wherein the client application is configured to transmit a bolus dosage command for configuring the fluid injection device to deliver the bolus delivery amount to the fluid injection device over the communications network.

17. The injection system of claim 15, wherein the client application is configured to generate a graphical user interface that includes a graphical user interface element that may be manipulated by a user to confirm the bolus delivery amount.

18. The injection system of claim 15, wherein the client application is configured to generate a graphical user interface that includes a graphical user interface element that may be manipulated by a user to adjust the bolus delivery amount.

19. The injection system of claim 15, wherein the client application is configured to generate a graphical user interface that includes a graphical user interface element that may be manipulated by a user to manually input a patient-specific parameter value and recursively determine the active amount of fluid in the body of the patient at the time for the bolus to be delivered based at least in part on the historical bolus data associated with previous boluses delivered to the patient using the patient-specific parameter value.

20. A method of operating a fluid injection device to deliver insulin to a patient, the method comprising:
receiving user input indicative of a desire to administer a bolus using the fluid injection device;
receiving, via a wireless network, one or more interstitial fluid glucose measurement values from an interstitial sensing arrangement including one or more interstitial sensing elements;
determining an adjusted glucose measurement value corresponding to a time for the bolus to be delivered in response to receiving the user input indicative of the desire to administer the bolus based at least in part on the one or more interstitial fluid glucose measurement values from the interstitial sensing arrangement;
recursively determining an active amount of the insulin in a body of the patient at the time for the bolus to be delivered based at least in part on historical bolus data associated with previous boluses delivered to the patient using the fluid injection device, by iteratively determining a plurality of intermediate values of active amount of fluid in the body of the patient associated with a plurality of intermediate times between (a) a most recent fluid delivery time and (b) the time for the bolus to be delivered, wherein each of the plurality of intermediate values of active amount of fluid in the body is determined for a particular intermediate time, from the plurality of intermediate times, that occurs after the most recent fluid delivery time and before the time for the bolus to be delivered;
after receiving the user input, determining a bolus delivery amount of the insulin based at least in part on the active amount of the insulin and a difference between the adjusted glucose measurement value and a target glucose value; and
determining a bolus dosage command for configuring the fluid injection device to deliver the bolus delivery amount.

* * * * *